United States Patent
Siddall et al.

(10) Patent No.: US 8,755,862 B2
(45) Date of Patent: Jun. 17, 2014

(54) SYSTEM AND METHOD FOR DETECTING PAIN AND ITS COMPONENTS USING MAGNETIC RESONANCE

(76) Inventors: Phillip John Siddall, Artarmon (AU);
Carolyn Mountford, East Ryde (AU);
Anne Woodhouse, Mandalong (AU);
Peter Stanwell, Cherrybrook (AU);
Rajmund Somorjai, Headingly (CA)

( * ) Notice: Subject to any disclaimer, the term of this patent is extended or adjusted under 35 U.S.C. 154(b) by 0 days.

(21) Appl. No.: 13/426,324

(22) Filed: Mar. 21, 2012

(65) Prior Publication Data
US 2012/0238862 A1 Sep. 20, 2012

Related U.S. Application Data

(63) Continuation of application No. 12/644,315, filed on Dec. 22, 2009, now abandoned, which is a continuation of application No. 10/844,297, filed on May 12, 2004, now Pat. No. 7,676,254.

(60) Provisional application No. 60/470,012, filed on May 12, 2003.

(51) Int. Cl.
*A61B 5/055* (2006.01)

(52) U.S. Cl.
USPC ........................................................ 600/410

(58) Field of Classification Search
USPC .......... 600/407, 410, 411, 427, 431, 473, 475
See application file for complete search history.

(56) References Cited

U.S. PATENT DOCUMENTS 7,676,254 B2 * 3/2010 Siddall et al. ................. 600/410

OTHER PUBLICATIONS

Grachev I, Fredrickson BE, Apkarian AV. Abnormal brain chemistry in chronic back pain: an in vivo proton magnetic resonance spectroscopy study. Pain 89 (2000) 7-18.*

* cited by examiner

*Primary Examiner* — Michael Rozanski
(74) *Attorney, Agent, or Firm* — Lucas & Mercanti, LLP; Peter J. Phillips

(57) ABSTRACT

A system and method identifies different components of the pain experience (nociceptive (tissue damage), neuropathic (nerve damage) and psychological) and their relative contributions by the use of magnetic resonance spectroscopy (MRS) to measure absolute and relative concentrations of metabolites in specific brain regions in the central nervous system or brain. The system and method can be used as a diagnostic tool for the assessment of the relative contribution of different aspects of the pain experience as well as monitoring of response to interventions directed at modifying these components.

4 Claims, 1 Drawing Sheet

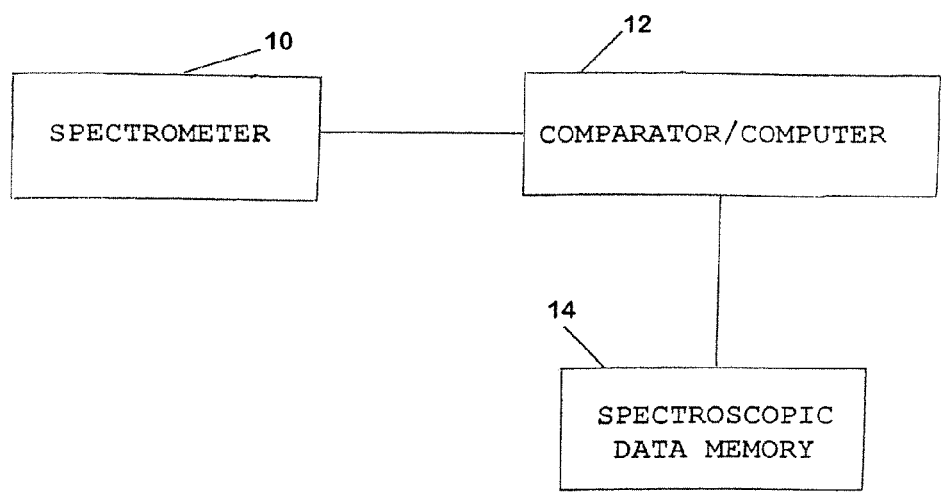

SYSTEM AND METHOD FOR DETECTING PAIN AND ITS COMPONENTS USING MAGNETIC RESONANCE

CROSS-REFERENCE TO RELATED APPLICATIONS

This application claims priority of U.S. Provisional Application Ser. No. 60/470,012 filed on May 12, 2003, incorporated by reference herein, and is a continuation of U.S. Ser. No. 10/844,297, which has issued as U.S. Pat. No. 7,676,254 on Mar. 9, 2010, and is a continuation of U.S. Ser. No. 12/644,315 filed Dec. 22, 2009.

BACKGROUND OF THE INVENTION

The present invention is directed to a system and method for detecting pain and its components using magnetic resonance spectroscopy (MRS).

Chronic pain is a major problem in our health care. The assessment of chronic pain is, however, limited by its subjective nature and the inability of any current diagnostic technique to objectively quantify any changes associated with the presence of pain per se.

Chronic pain has an enormous impact both in terms of individual suffering and economic impact through use of health care resources and reduced ability to engage in work and other activities and treatment. However, the assessment of pain and the subsequent use of treatment is largely based on subjective report by the patient.

Chronic pain is one of the most common and yet difficult to treat of conditions. It has traditionally been regarded merely as a symptom of pathology. This concept has served well in an acute pain model where treatment is directed at treating pathology and when there is resolution of pain with subsequent healing. However the model has not worked well in the chronic pain situation. In this situation, ongoing pathology, as in arthritis or nerve injury, may give rise to ongoing pain and may not be treatable with currently available remedies. Even more difficult, in many situations there is ongoing pain with no identifiable pathology that may be the cause for persistent pain. In these situations particularly psychological factors may be invoked as an explanation for ongoing pain that is resistant to treatment. Although it is now recognized that a psychological origin for pain, i.e., hysteria or malingering, is uncommon, it is also recognized that psychological factors have an important role in the presentation of any pain. Pain has three distinct but overlapping components: nociceptive, neuropathic and psychological. All of these may contribute in varying degrees to a person's perception and expression of pain.

Nociceptive pain is the most common type of pain and is believed due to signals arising from pathology in body tissues. Thus, appendicitis, kidney stones and joint inflammation in arthritis all give rise to increased inputs from the structures affected and this is perceived as pain. Although there may be modification of these inputs (either up or down) by physiological processes in the brain and spinal cord, basically pain is due to increased inputs arriving in the central nervous system. A subject usually responds to treatments that reduce these inputs such as nerve blockade, analgesics, anti-inflammatories or psychological treatments that increase levels of inhibition and thereby reduce inputs.

In distinction to nociceptive pain, the second pain component, neuropathic pain, occurs as a result of damage to the peripheral or central nervous system. In its strictest definition, this type of pain occurs in the presence of features of neurological dysfunction such as sensory or motor deficits. It has different features and is often described as shooting, electric, burning or shock-like. It may be difficult to detect pathology with current imaging techniques. It generally responds poorly to the strategies used for the treatment of nociceptive pain such as analgesics, anti-inflammatories and nerve blockade or even section. This type of pain responds better to strategies that reduce inputs due to nerve damage such as discharges arising from neuromas or to drugs that increase the level of inhibition in the central nervous system.

The third pain component, the psychological component, is a universal contribution to our experience of pain. Psychological processes can influence both pain perception and pain expression (disability) in an upward or downward reaction. For example, during a sports match, many athletes will not notice or disregard a sometimes severe injury so that both pain and disability are minimal in the face of quite large inputs from damaged structures. Conversely, mood changes such as anxiety or depression or learned processes such as fear-avoidance may enhance both the perception of pain and associated disability.

Although it is widely recognized that these processes are at work in people with pain, it is currently extremely difficult to determine the relative contribution of each of these three pain components to a person's presentation. This is despite the fact that many of the treatments currently available depend on accurate diagnosis of the type of pain present. As mentioned, the treatments for nociceptive and neuropathic pain are quite different and have little value when used for the wrong conditions. Psychological treatments can be used for both types of pain. However, current psychological treatments are directed more towards addressing disability and the ability to cope with pain than with changing pain perception itself. However, in some people in whom negative psychological processes are active, recognition of this would help direct treatment towards addressing these issues rather than a search for a nociceptive or neuropathic focus that may be relatively minor.

Thus, the best treatment for pain depends on a accurate assessment of the different components that contribute towards someone's sensation of pain. Current diagnostic techniques are unreliable and give limited information. Many diagnostic techniques are unable to accurately identify sources that may be giving rise to nociceptive or neuropathic pain. Even if damage to an intervertebral disc or nerve root, for example, can be demonstrated, it is extremely difficult to determine with any confidence that even this structural abnormality is giving rise to pain. It is also difficult to determine the relative contribution of psychological factors. Although there are a number of tests that can assess pain perception, mood, motor disability and cognitions, it is still difficult to determine to what extent these changes are contributing to a person's pain presentation.

There is therefore a huge need for a system and method that can objectively and accurately assess the relative contributions of each of the components to a person's pain. Current instruments are largely reliant on subjective self report. An objective method of reliably detecting changes associated with pain perception would enhance both the assessment and treatment of pain. If the techniques could also assess the relative contributions of the different pain components (nonciceptive, neuropathic and psychological), this would revolutionize pain medicine.

One study has reported that low back pain is associated with a decrease in glucose in the frontal cortex as well as an increase in glucose in the thalamus. (Grachev, I. D., Fredrickson, B. E., and Apkarian, A. V. Abnormal brain chemistry in chronic back pain: an in vivo proton magnetic resonance spectroscopy study. Pain 89:748, 2000). This article is incorporated by reference herein.

Another study reported biochemical changes in several brain regions in a small number of subjects with low back pain and pain following spinal cord injury. (Pattany, P. M., et al., Proton magnetic resonance spectroscopy of the thalamus in patients with chronic neuropathic pain after spinal cord injury, Am. J. Neuroradiol., 23:901-905, 2002). This article is incorporated by reference herein.

However, there is currently no objective means of detecting the components or types of pain.

SUMMARY OF THE INVENTION

The detection and characterization of biochemical changes associated with chronic pain would benefit our understanding of the pathophysiology of chronic pain as well as providing an objective measure that correlates with the presence of pain.

MRS is a technique that is currently used for the characterization of the chemical profile of body tissues. This can be done with samples of tissues such as breast or prostate that have been removed from the body (ex vivo) and tissues still inside the body such as the brain (in vivo). Neurospectroscopy, in vivo, can document changes in brain chemistry associated with a range of pathologies. In vivo spectroscopy therefore offers the ability to characterize the biochemical profile of an area of the brain without the need to remove tissue or to perform an invasive procedure. It has already proved useful for the diagnosis of brain tumors and infections. More recent work, however, suggests that MRS may also detect changes associated with brain dysfunction such as epilepsy or dyslexia. It even appears to detect brain changes associated with normal function such as transient changes in glucose following light stimulation of the eyes. Therefore, MRS provides a potentially useful tool in the assessment of brain changes associated with pain. These may either be "normal" changes in response to pain as a sensory input or "abnormal" changes in response to persistent pain either with nociceptive or neuropathic pain. It may also be possible that it may detect changes associated with psychological aspects of pain.

Studies of the brain using functional imaging techniques have identified a number of brain regions that are involved in pain processing. These include the somatosensory cortex, anterior cingulated cortex, prefrontal cortex, insular cortex and thalamus. Therefore, biochemical changes associated with pain may be detected in these regions. Chronic pain may be associated with biochemical changes in some of the regions. Other pain states may share these changes and chronic pain may be associated with neural degeneration.

According to the present invention, neurospectroscopy of the human brain can detect whether the person is experiencing pain and the type and possibly the intensity of the pain, distinguish the components contributing to the pain (nociceptive, neuropathic and psychological), assign differences in the chemical species giving rise to the pain and the origin, and identify different biochemical mechanisms associated with pain and the origin of the pain. These results can be used to guide patient management and monitor patient outcome.

According to the present invention, a method of detecting at least one component of pain being experienced by a subject is provided, comprising obtaining spectroscopic data of the brain of a subject experiencing pain, and comparing the spectroscopic data obtained with reference spectroscopic data having characteristic values which correlate with and identify at least two different pain components, to detect the presence of at least one pain component being experienced by the subject.

The present invention also provides an apparatus for detecting at least one component of pain being experienced by a subject, comprising a magnetic resonance spectrometer for obtaining spectroscopic data of the brain of a subject experiencing pain, a memory device for storing reference spectroscopic data having characteristic values which correlate with and identify at least two different pain components, and a comparator which compares the spectroscopic data obtained with the reference spectroscopic data to detect the presence of at least one pain component being experienced by the subject.

The present invention also provides a method of detecting whether a subject is experiencing a nociceptive pain component, comprising obtaining spectroscopic data of brain regions in the subject to determine the concentrations of a selected biochemical, and comparing the biochemical concentration obtained with a reference biochemical concentration, whereby a difference in selected biochemical concentration relative the reference biochemical concentration is indicative of the presence of nociceptive pain.

BRIEF DESCRIPTION OF THE DRAWING

The FIGURE is a schematic block diagram illustrating components of a system which may be used to practice the apparatus and method according to the invention.

DETAILED DESCRIPTION OF THE INVENTION

According to the present invention, a method of detecting at least one component of pain being experienced by a subject is provided, comprising obtaining spectroscopic data of the brain of a subject experiencing pain, and comparing the spectroscopic data obtained with reference spectroscopic data having characteristic values which correlate with and identify at least two different pain components, to detect the presence of at least one pain component being experienced by the subject.

The at least two different pain components may be at least two of nociceptive, neuropathic and psychological pain components.

The at least two different pain components most preferably comprise all three of nociceptive, neuropathic and psychological pain components.

The step of comparing preferably comprises comparing spectroscopic data with reference spectroscopic data to determine relative contributions of the pain components being experienced by the subject.

The present invention also provides an apparatus for detecting at least one component of pain being experienced by a subject, comprising a magnetic resonance spectrometer for obtaining spectroscopic data of the brain of a subject experiencing pain, a memory device for storing reference spectroscopic data having characteristic values which correlate with and identify at least two different pain components, and a comparator which compares the spectroscopic data obtained with the reference spectroscopic data to detect the presence of at least one pain component being experienced by the subject.

The different pain components are preferably at least two of nociceptive, neuropathic and psychological pain components.

The different pain components most preferably comprise all three of nociceptive, neuropathic and psychological pain components.

The comparator preferably determines the relative contribution of each of the pain components being experienced by the subject.

The present invention also provides a method of detecting whether a subject is experiencing a nociceptive pain component, comprising obtaining spectroscopic data of brain regions in the subject to determine the concentrations of a selected biochemical, and comparing the biochemical concentration obtained with a reference biochemical concentration, whereby a difference in selected biochemical concentration relative the reference biochemical concentration is indicative of the presence of nociceptive pain.

The brain region may be the prefrontal cortex. The selected biochemical may be glucose, wherein the selected direction is an increase.

The selected biochemical may be GABA, wherein the selected direction is an increase.

The selected biochemical may be N-acetylaspartate (NAA) and wherein the selected direction is a decrease.

The selected biochemical may be choline and wherein the selected direction is an increase.

According to the present invention, a study was performed to determine whether MRS can be used as an identifier to different pain components. The study included an examination of the prefrontal cortex, anterior cingulated cortex and thalamus of patients who reported low back pain and pain following spinal cord injury. As a result of the study patterns were found which enable one to distinguish different pain components. The first pattern is a relative increase in glucose and the inhibitory chemical GABA in prefrontal cortex. The second pattern is a relative decrease in glucose and GABA in the prefrontal cortex. The third pattern is a relatively small and sometimes insignificant change in glucose and GABA despite a similar pain report.

The changes observed here do not correspond to the suggestion by Grachev et al. that pain is associated only with a decrease in prefrontal glucose. People with pain can exhibit either an increase or a decrease in glucose and therefore the direction of change (increase or decrease) is not the determinant of the presence of pain. The findings demonstrate is that those who have either an increase or a decrease in glucose may have pain, with the direction of the change indicating the type of pain.

Further examination of the two groups reveals other patterns. The group with an increase in prefrontal glucose also has a relatively high concentration of N-acetyl aspartate (NAA) and a low concentration of choline. Conversely, the group with a decrease in prefrontal glucose has relatively low NAA and high choline. The groups can be further distinguished according to neurological findings, imaging and response to treatment. Those with increased glucose have pain that is more often confined to the back without radiation and respond to nerve blocks of back structures. Those with decreased prefrontal glucose have neurological deficits, nerve root impingement on imagining and/or positive response to treatments that help neuropathic pain. Therefore, it was concluded that both groups have pain, both groups have changes in prefrontal glucose, but the direction of change (increase or decrease) is related to the strength of inputs arriving in the brain. Those with no nerve injury and pain have increased inputs (as generally happens in nociceptive pain) with an increase in glucose and GABA. Those with nerve injury and loss of inputs (as generally happens in neuropathic pain) have a decrease in prefrontal glucose and GABA. The reason for the difference in findings, therefore, of Grachev et al. and the reason that they suggested that pain is due to a decrease in glucose is that most of their subjects had low back pain which was predominantly neuropathic in nature. This is supported by the fact that all their subjects has radiation of pain to the legs and most had disc herniation and surgery.

The third group with little or no change in prefrontal glucose or GABA were examined further. Nearly all subjects demonstrated changes in mood that were linearly related to pain intensity. However, the distinguishing characteristic of those with little change was that their mood dysfunction was disproportionate to their reported pain severity. Therefore it appears that this group may have pain but that psychological factors play a large role in their pain presentation.

One other important finding was made. Not only were changes in glucose (positive or negative) found in those with pain, but these changes were linearly correlated with pain intensity (visual analog score). Therefore, it is possible that this method can not only distinguish whether different factors are important contributors to pain, it may also give an indication of the relative contribution of each pain component and their role in the presentation of pain.

Neuro spectroscopy in the region of the thalamus can identify the presence of pain with a high level of accuracy. A group of subjects with low back pain (N=31) was compared to a group of controls (N=35), as well as a preliminary study in a small number of subjects with spinal cord injury, show the MRS data when analyzed by a statistical classification strategy (SCS) gives an accuracy of 96%. The SCS can be of the basic type described in Wallace J C et al. (Classification of .sup.1H MR Spectra of Biopsies from Untreated and Recurrent Ovarian Cancer Using Linear Discriminant Analysis. Magn Reson Med 1997; 38:569-76) or a more robust type as described in PCT WO 01/28412 A1 (PCT/CA00/01238) wherein the cross-validation step is repeated a plurality of times, each time selecting a different portion of the spectra. These studies indicate significant differences in neurotransmitter and metabolite concentrations in the brain regions examined when pain patients are compared with controls and between different pain conditions will allow the origin and intensity of the pain to be recorded as well.

Table 1 shows the results of a study of a group of patients with lower back pain and controls with no back pain. Using six regions using only crisply classified spectra for sensitivity, specificity and accuracy yielded the following results:

| Anatomical Region of the Brain | Crispness | Sensitivity | Specificity | Accuracy % |
|---|---|---|---|---|
| thalamus anterior cingulate cortex prefrontal cortex | 85% | 96% | 100% | 98% |

The location in the body where the patient is experiencing pain can often be identified by patient report. The value of the described diagnostic technique is that once a region has been identified the response of the brain can be determined and the change in biochemical profile used to determine the relative contributions of these different pain components. This may provide the practitioner with an objective assessment of the contribution of these different components and provide clear direction for the management.

As mentioned above MRS is able to identify the relative concentrations in brain regions and it has been demonstrated that neuropathic pain is associated with a decrease in the concentration of the inhibitory chemical GABA in specific brain regions. This appears to indicate that this reduction in the chemical is associated with a reduction in inhibition and subsequent amplification of pain signals. This suggests that interventions that address this chemical deficit may be effective in treating this condition. Therefore, MRS may a useful diagnostic tool in the determination of specific chemical deficits in the brain and this information can be used to indicate effective treatment. It also means that MRS can be used to monitor progress as treatment is instituted.

The development of neurospectroscopy as a non-invasive, painless, "diagnostic" test in the assessment of chronic pain would have a huge impact on clinical practice by providing an objective indicator of pain. This would benefit the assessment of chronic pain, allow matching treatment progress.

The invention may be implemented with the system shown in the FIGURE which shows a spectrometer 10 for obtaining spectral data of brain regions, and a comparator/computer 14 which compares the spectral data obtained with reference spectroscopic data stored in a memory 14, to detect one or more of the pain components of a subject under examination.

Although one embodiment of the invention has been shown and described, changes will occur to those skilled in the art, and the invention is defined by way of the claims and not by the single embodiment.

We claim:

1. An apparatus for detecting whether a subject is experiencing any of three individual pain components of nociceptive pain, neuropathic pain, or psychological pain, comprising:
   a magnetic resonance spectrometer configured for obtaining spectroscopic data of the brain of a subject experiencing pain;
   a memory device configured for storing reference spectroscopic data having characteristic values which correlate with and identify the three different pain components; and
   a comparator configured to compare the spectroscopic data obtained with the reference spectroscopic data to detect whether the subject is experiencing any of the three individual pain components (1) wherein an increase of glucose and GABA in the frontal cortex, or a decrease in N-acetylaspartate (NAA), or an increase in choline, indicates nociceptive pain, (2) wherein a decrease of glucose and GABA in the frontal cortex indicate neuropathic pain, and (3) a small variation of glucose or GABA in the frontal cortex indicates psychological pain.

2. The apparatus of claim 1, wherein the comparator determines the relative contribution of each of the pain components being experienced by the subject.

3. A method of detecting components of pain being experienced by a subject, comprising:
   obtaining spectroscopic data with a magnetic resonance spectrometer of brain regions in the subject to determine the concentration of selected biochemicals and
   comparing the spectroscopic data obtained with reference spectroscopic data having characteristic values which correlate with and identify individually three pain components of nociceptive, neuropathic and psychological pain to detect the presence of which of the three pain components are being experienced by the subject (1) wherein an increase of glucose and GABA in the frontal cortex, or a decrease in N-acetylaspartate (NAA), or an increase in choline, indicate nociceptive pain, (2) wherein a decrease of glucose and GABA in the frontal cortex indicates neuropathic pain, and (3) a small variation of glucose or GABA in the frontal cortex indicates psychological pain.

4. The method of claim 3, wherein the step of comparing comprises comparing spectroscopic data with reference spectroscopic data to determine relative contributions of the three pain components being experienced by the subject.

\* \* \* \* \*